(12) United States Patent
Dosho

(10) Patent No.: US 6,285,736 B1
(45) Date of Patent: Sep. 4, 2001

(54) METHOD FOR X-RAY MICRO-DIFFRACTION MEASUREMENT AND X-RAY MICRO-DIFFRACTION APPARATUS

(75) Inventor: Akihide Dosho, Tokyo (JP)

(73) Assignee: Rigaku Corporation, Akishima (JP)

( * ) Notice: Subject to any disclaimer, the term of this patent is extended or adjusted under 35 U.S.C. 154(b) by 0 days.

(21) Appl. No.: 09/427,618

(22) Filed: Oct. 27, 1999

(30) Foreign Application Priority Data

Nov. 13, 1998 (JP) ................................................ 10-323538

(51) Int. Cl.$^7$ ................................................ G01N 23/207
(52) U.S. Cl. ................................ 378/79; 378/71; 378/73; 378/81; 378/83
(58) Field of Search ........................ 378/46, 70, 71, 378/73, 79, 81, 83

(56) References Cited

U.S. PATENT DOCUMENTS

| | | | |
|---|---|---|---|
| 3,394,255 | * 7/1968 | Furnas, Jr. | 378/71 |
| 3,564,240 | * 2/1971 | Thomas, Jr. | 378/81 |
| 4,076,981 | * 2/1978 | Sparks et al. | 378/71 |
| 4,412,345 | * 10/1983 | Workman et al. | 378/78 |
| 4,710,259 | * 12/1987 | Howe et al. | 117/15 |
| 5,359,640 | * 10/1994 | Fink et al. | 378/79 |

* cited by examiner

*Primary Examiner*—Robert H. Kim
*Assistant Examiner*—Allen C. Ho
(74) *Attorney, Agent, or Firm*—Burns, Doane, Swecker & Mathis, LLP

(57) ABSTRACT

An X-ray micro-diffraction measuring method for detecting X-rays diffracted at a minute portion of a specimen upon irradiating the minute portion with X-rays is disclosed. A cylindrical stimulation type fluorescent member is arranged around the specimen. A sample facet of the specimen is tilted by, for example, 45° with respect to the stimulation type fluorescent member such that the stimulation type fluorescent member can receive both diffracted X-rays passing along a direction tangential to the sample facet and diffracted X-rays passing along a direction perpendicular to the sample facet. Diffracted X-ray images can be obtained on the stimulation type fluorescent by merely rotating the specimen about only the $\phi$ axis thereof so as to perform the in-plane rotation without a rotation about the $\chi$ axis. By eliminating a rotation about one axis from rotations about two axes for the specimen, it may be possible to avoid a degradation of measurement preciseness due to a crossing error of the two axes. Also, the elimination of the axis mentioned above may cause the structure of the apparatus to be simplified and the time required for the measurement to be shortened.

14 Claims, 5 Drawing Sheets

METHOD FOR X-RAY MICRO-DIFFRACTION MEASUREMENT AND X-RAY MICRO-DIFFRACTION APPARATUS

BACKGROUND OF THE INVENTION

1. Field of the Invention

The present invention relates to a method for X-ray micro-diffraction measurement in which diffracted X-rays occurred at a minute portion of a specimen upon irradiating the minute portion with X-rays. Also, The present invention relates to an apparatus for performing the same method.

2. Description of the Related Art

In the X-ray measurement in which a specimen containing a large number of crystal grains, that is, a polycrystal specimen, is irradiated with X-rays having large cross sectional beam diameter, a large number of crystal grains exist in an area which is to be irradiated by the X-rays. Therefore, a large number of crystal grains in that area comes to satisfy the diffraction condition, so that a large number of crystal grains can direct diffracted X-rays to an X-ray detector arranged in a predetermined position relative to the specimen. In this case, it is possible to detect diffracted X-rays by the X-ray detector arranged in a fixed position.

However, there may be a case where it is necessary to know a diffracted X-ray information for a minute sample or a minute area of a polycrystal specimen, which may be not more than 100 $\mu$m in diameter. In such case, an irradiation field of X-rays becomes narrow, so that the number of crystal grains contained in such narrow area becomes small. Therefore, regardless of crystal grains at which the X-ray diffraction occur, detection of diffracted X-rays by an X-ray detector arranged in a fixed position becomes impossible frequently.

Further, there may be a case where only one crystal grain exists in the field of X-ray irradiation, that is, a case of single crystal, in which diffraction of X-rays occurs at a specific diffraction angle. In a case where a few crystal grains exist within the X-ray irradiation field, including the case of the single crystal condition, Debye ring formed by diffracted X-rays may not be found unless a sample is swung.

An X-ray micro-diffraction apparatus, which makes an X-ray diffraction measurement for a minute portion of a specimen possible, includes rotary systems rotatable about at least independent two axes, which are usually called as a $\chi$ axis and a $\phi$ axis, respectively, and cross with each other at an irradiation point of X-rays. A specimen is supported by those rotary systems and is rotated about the orthogonal two axes independently by the rotary systems during the minute portion thereof is irradiated with X-rays.

Such independent rotations of the specimen about the two axes disorders directional distribution of crystal lattice planes of crystal grains with respect to the incident X-rays. As a result, X-rays diffracted by these crystal grains can be detected by the X-ray detector arranged in a constant position even if there is few crystal grains exist in an irradiation area of X-rays of the specimen.

The X-ray micro-diffraction apparatus for detecting diffracted X-rays from the minute portion of the specimen can be constructed as shown in, for example, FIG. 3. In FIG. 3, the $\chi$ axis is set coincident with an optical axis X0 of X-rays 'R' and a $\phi$ rotary device 51 is arranged on the $\phi$ axis line. The $\phi$ rotary device 51 rotates a $\phi$ arm 52 about the $\phi$ axis. The $\phi$ arm 52 supports an $\omega$ rotary device 53 which rotates an $\omega$ arm 54 about the $\omega$ axis which is orthogonal to the $\chi$ axis, that is, the optical axis X0 of X-rays 'R'.

The $\omega$ arm 54 supports a $\phi$ rotary device 56 which rotates the specimen 'S' about the $\phi$ axis so as to rotate in a plane. The $\phi$ axis is contained in a plane which contains the X-ray optical axis XO and is orthogonal to the $\omega$ axis, and also passes through a cross point of the $\omega$ axis and the $\chi$ axis. The specimen 'S' is arranged at the cross point of the $\chi$ axis, the $\omega$ axis and the $\phi$ axis, to thereby be located on an irradiation point of X-rays 'R'.

A curved PSPC, namely, a position sensitive proportional counter 57 is arranged as the X-ray detector in a position remote from the specimen 'S', by an appropriate distance. The PSPC 57 detects a time difference between pulses generated at opposite ends of a core line of a PC, namely, a proportional counter so that a position resolution can be obtained in a direction of the core line of the PC, that is, in a linear line. In FIG. 3, the position resolution is given in the linear direction within a plane orthogonal to the $\omega$ axis, so that X-rays having different diffraction angles are detected simultaneously along the linear direction.

In the X-ray micro-diffraction apparatus mentioned above, the specimen 's' is rotated about the $\chi$ axis and the $\phi$ axis independently, so that an arbitrary minute portion of the specimen 'S' can be brought to the irradiation point of X-rays 'R'. Therefore, the PSPC 57 can detect all of X-rays diffracted at the specimen 'S'.

The specimen 'S' is rotated about the $\omega$ axis in order to regulate the incident angle of X-rays to the specimen 'S'. After the incident angle is set to a predetermined value, for example, 20° to 30°, the specimen 'S' is fixed in the position around the $\omega$ axis.

In the device shown in FIG. 3, the $\chi$ axis is set coincident with the optical axis X0 of X-rays and the $\omega$ axis rotary system is mounted on the $\omega$ axis rotary system. However, the X-ray micro-diffraction apparatus may have another construction such as shown in FIG. 4, in which the $\chi$ axis rotary system is mounted on the $\omega$ axis rotary system so that the $\chi$ axis is not always coincident with the optical axis X0 of X-rays.

In any way, the conventional X-ray micro-diffraction apparatus for a minute portion of a specimen requires at least two rotary systems, namely, the $\chi$ axis rotary system and the $\phi$ axis rotary system, resulting in a complicated construction.

Further, when the cross point of these two axes is not exactly defined to thereby cause a crossing error between these two axes, the irradiation field of X-rays on the specimen 'S' is broadened, causing the measurement of diffracted X-rays at a minute portion of the specimen to be meaningless. Therefore, the positional relation between these two axes must be severely regulated. However, such precise regulation of the positional relation has been very difficult.

Further, since the PSPC 57 is a one-dimensional detector, it is necessary to rotate the specimen 'S' about the $\chi$ axis in order to detect X-rays diffracted by the specimen 'S', causing a time required for the X-ray diffraction measurement to be long.

SUMMARY OF THE INVENTION

The present invention was made in view of the state of art and has an object to provide an X-ray micro-diffraction measuring method and an apparatus for the same method, which are capable of eliminating one rotary axis from two rotary axes employed in conventional method.

Another object of the present invention is to avoid a degradation of the preciseness of an X-ray diffraction measurement caused by a crossing error between two rotary axes. Another object of the present invention is to simplify the construction of an X-ray diffraction apparatus. A further object of the present invention is to shorten an X-ray diffraction measuring time.

These objects are achieved by the present invention, which is as follow:

(1) An X-ray micro-diffraction measuring method for detecting X-rays diffracted at a minute portion of a specimen irradiated with X-rays comprising the steps of arranging a cylindrical two-dimensional X-ray detector around the specimen and tilting a surface of the specimen with respect to the two-dimensional X-ray detector in such a manner that both diffracted X-rays diffracted by the specimen so as to pass along a direction tangential to a sample facet of the specimen and diffracted X-rays diffracted by the specimen so as to pass along a direction perpendicular to the sample facet of the specimen are simultaneously received by the two-dimensional X-ray detector.

There have been known the so-called zero-dimensional X-ray detector such as a PC or a SC, namely, scintillation counter, which receives X-rays at a point. Also, there have been known the so-called one-dimensional X-ray detector such as a PSPC, which receives X-rays in a linear line. Unlike the aforesaid X-ray detectors, the two-dimensional X-ray detector used in the present invention detects X-rays at arbitrary point in a plane. An X-ray film, a stimulation type fluorescent member and the like may be given as examples of the two-dimensional X-ray detector mentioned above.

According to the X-ray micro-diffraction measuring method constructed as mentioned above, it is possible to detect all of X-rays diffracted at the minute sample portion of the specimen by rotating the specimen in a plane, that is, about only the $\phi$ axis without a rotation about the $\chi$ axis employed in the prior art.

It has been conventional in the X-ray measurement that the specimen has to be rotated about both the $\chi$ axis and the $\phi$ axis. Therefore, the irradiation field of X-rays on the specimen tends to be broadened due to the crossing error between the two axes, so that it is impossible to precisely irradiate the minute sample portion of the specimen with X-rays. On the contrary, the present invention which does not require the $\chi$ axis makes possible to avoid degradation of the preciseness of measurement due to the broadening of the irradiation field of X-rays.

Also, since one of the rotary systems for the specimen can be removed in the present invention, it is possible to simplify the structure of the device. Further, since the present invention utilizes the two-dimensional X-ray detector, it is possible to shorten the measuring time compared with the case where the zero-dimensional X-ray detector or the one-dimensional X-ray detector is employed alternatively.

(2) the X-ray micro-diffraction measuring method mentioned above may preferably have the stimulation type fluorescent member as the two-dimensional X-ray detector. The stimulation type fluorescent member is a radioactive ray detector of energy storage type, which is formed by painting a surface of a flexible film, a flat plate film or other member with fine crystals of, for example, $BaFBr:Er^{2+}$. The stimulation type fluorescent member can store X-rays, etc., as energy thereof and then discharge the energy externally by irradiating it with stimulated light such as laser light, etc.

In other words, when the stimulation type fluorescent member is irradiated with X-rays, etc., energy thereof is stored in an irradiated portion of the stimulation type fluorescent member to thereby form a latent image therein.

Subsequently, when the stimulation type fluorescent member is irradiated with the stimulated light such as laser light, etc., the latent image energy is discharged externally as light. By detecting the discharged light by a photoelectric tube, it is possible to measure both the diffraction angle and the intensity of X-rays having attributed the formation of the latent image. This stimulation type fluorescent member has sensitivity 10 to 60 times that of the conventional X-ray film and a wide dynamic range from $10^5$ to $10^6$.

(3) In the X-ray micro-diffraction measuring method mentioned above, the sample facet of the specimen is preferably tilted with respect to a center axis of the two-dimensional X-ray detector by an angle of about 45°. Thus, it is possible to reliably detect, by the two-dimensional X-ray detector, both diffracted X-rays diffracted by the specimen so as to pass along a direction tangential to the sample facet and diffracted X-rays diffracted by the specimen so as to pass in a direction perpendicular to the facet surface.

(4) When the specimen is irradiated with X-rays, both diffracted X-rays and fluorescent X-rays are generated. The diffracted X-rays are generated on the basis of the fact that X-rays which are selected to satisfy a specific condition, that is, Bragg's diffraction condition among X-rays reflected by crystal lattice plane of the specimen are increased, while the other X-rays are not observed by mutual cancellation. Such a diffracted X-rays are generated in relation to the atomic arrangement of the crystal.

On the other hand, each of the atoms constituting the specimen has a specific order of electron shells. When such specimen is irradiated with radioactive ray such as X-rays, γ-rays or electron beams, X-rays having property specific for the specimen, that is, specific X-rays, are generated. Thus generated X-rays are generally referred to as fluorescent X-rays, which are generated in relation to both the kind and amount of atoms existing in the specimen.

According to the present invention, since the two-dimensional X-ray detector having a cylindrical shape is employed in the X-ray micro-diffraction measuring method for a minute portion of the specimen, it is possible to form an opening at the edge portion of the two-dimensional X-ray detector. Accordingly, by arranging a semiconductor X-ray detecting element in the opening, fluorescent X-rays comes to be measured simultaneously with the diffracted X-ray measurement. Thus, it is possible to perform an analysis related to atoms contained in the specimen together with an analysis of the crystal structure of the specimen.

With the semiconductor X-ray detecting element being arranged in the opening formed at the edge portion of the cylindrical two-dimensional X-ray detector, the detecting element can take its input portion for X-rays to a position which is very close to the specimen and is at a low angle with respect to a normal line of the surface of the specimen. Therefore, the detecting element can receive the fluorescent X-rays in a large range of divergence angle. Further, since the path of X-rays in the specimen becomes short, the influence of absorption is reduced, so that it is possible to perform an efficient fluorescent X-ray analysis.

In the above-mentioned construction, the semiconductor X-ray detecting element can be constructed with the so-called SSD, namely, a solid state detector. Contrary to the X-ray detector such as an ionization chamber or a PC, etc., which utilizes the ionization of gas due to radioactive ray, the SSD utilizes ionization of a solid material, namely, a semiconductor.

When X-rays are incident on a silicon semiconductor or a germanium semiconductor, ion pairs, namely, electron-hole pairs are produced. The number of ion pairs is proportional to a quantum energy of the incident X-rays. These electrons and holes are separated to a positive and a negative pole, respectively, resulting in a pulse current. The pulse current has a pulse height corresponding to the amount of energy of the incident X-rays, so that it is possible to measure the amount of energy of the incident X-rays, that is, the wavelength of the X-rays.

An energy distribution measuring device such as a MCA, namely, a multi-channel pulse height analyzer is usually connected to an output terminal of the semiconductor X-ray detecting element such as the SSD. A single channel pulse height analyzer, which is used generally as the energy distribution measuring device, analyzes an input pulse signal on the basis of whether or not a height of the input pulse signal is within a window having a predetermined width. On the other hand, the MCA is constructed by arranging a plurality of such single channel pulse height analyzers with different window widths to classify the input X-rays on the basis of the amount of energy thereof, that is, the wavelength thereof.

(5) An X-ray micro-diffraction apparatus for detecting X-rays diffracted at a minute sample portion of a specimen by irradiating the minute sample portion with X-rays comprises a two-dimensional X-ray detector arranged around the specimen, $\phi$ rotary means for rotating the specimen within a plane, tilting means for tilting a surface of the specimen with respect to the two-dimensional X-ray detector and $\omega$ rotary means for rotating the specimen to change an incident angle of X-rays to the specimen.

According to this X-ray micro-diffraction apparatus in which the two-dimensional X-ray detector is used as the X-ray detector and the sample facet is tilted under the above mentioned specific condition, it is possible to detect all of the X-rays diffracted at the minute portion of the specimen by rotating the specimen in the plane, that is, about the $\phi$ axis without requiring the rotation of the specimen about the $\chi$ axis, which is required in the conventional X-ray diffraction device.

As mentioned previously, the specimen has to be rotated about the $\phi$ axis and about the $\chi$ axis in the conventional X-ray measurement. Therefore, the field to be irradiated by X-rays tends to be broadened due to the crossing error of these axes, so that it becomes difficult to irradiate precisely the minute portion of the specimen with X-rays. Contrary to the conventional X-ray measurement, the degradation of preciseness of the X-ray measurement due to the broadening of the X-ray irradiation field can be avoided in the present invention since there is no $\chi$ axis.

Also, since one of the rotary systems for the specimen can be eliminated in the present invention, the X-ray micro-diffraction apparatus is easily constructed. Further, since the two-dimensional X-ray detector is used in the present invention, it is possible to shorten the time required for the measurement compared with the case where the zero-dimensional X-ray detector or the one-dimensional X-ray detector is employed.

(6) In the above mentioned X-ray micro-diffraction apparatus according to the present invention, the two-dimensional X-ray detector is preferably formed by a stimulation type fluorescent member.

(7) Further, in the above mentioned X-ray micro-diffraction apparatus according to the present invention, it is preferable that the tilting means tilts the sample facet of the specimen with respect to a center axis of the stimulation type fluorescent member by an angle of about 45°. Thus, the two-dimensional X-ray detector can reliably detect both the diffracted X-rays passing in a direction tangential to the sample facet and the diffracted X-rays passing in a direction perpendicular to the sample facet.

(8) The X-ray micro-diffraction apparatus of the present invention can further comprise an opening formed at the end portion of the cylindrical two-dimensional X-ray detector, a semiconductor X-ray detecting element provided in the opening which receives fluorescent X-rays so as to output a signal corresponding to an amount of energy of the fluorescent X-rays, and an energy distribution measuring device responsive to the output signal from the semiconductor X-ray detecting element for obtaining an energy distribution of the fluorescent X-rays.

With the construction of the X-ray micro-diffraction apparatus mentioned above, it is possible to perform the fluorescent X-ray measurement by means of the semiconductor X-ray detecting element simultaneously with the X-ray diffraction measurement. Thus, it is possible to perform an analysis related to atoms contained in the specimen, in addition to the crystal structure analysis of the specimen.

Further, when providing the semiconductor X-ray detecting element in the opening formed at the edge of the two-dimensional X-ray detector, the semiconductor X-ray detecting element can take its input portion for X-rays to a position being close to the specimen and being at a small angle with respect to a normal line of the sample face. As a result, the detecting element comes to receive fluorescent X-rays within a large divergence angle. Further, since the path of X-rays within the specimen becomes short, the influence of absorption is reduced and an efficient fluorescent X-ray analysis can be performed.

DETAILED DESCRIPTION OF THE PREFERRED EMBODIMENTS (First Embodiment)

Figure 1:
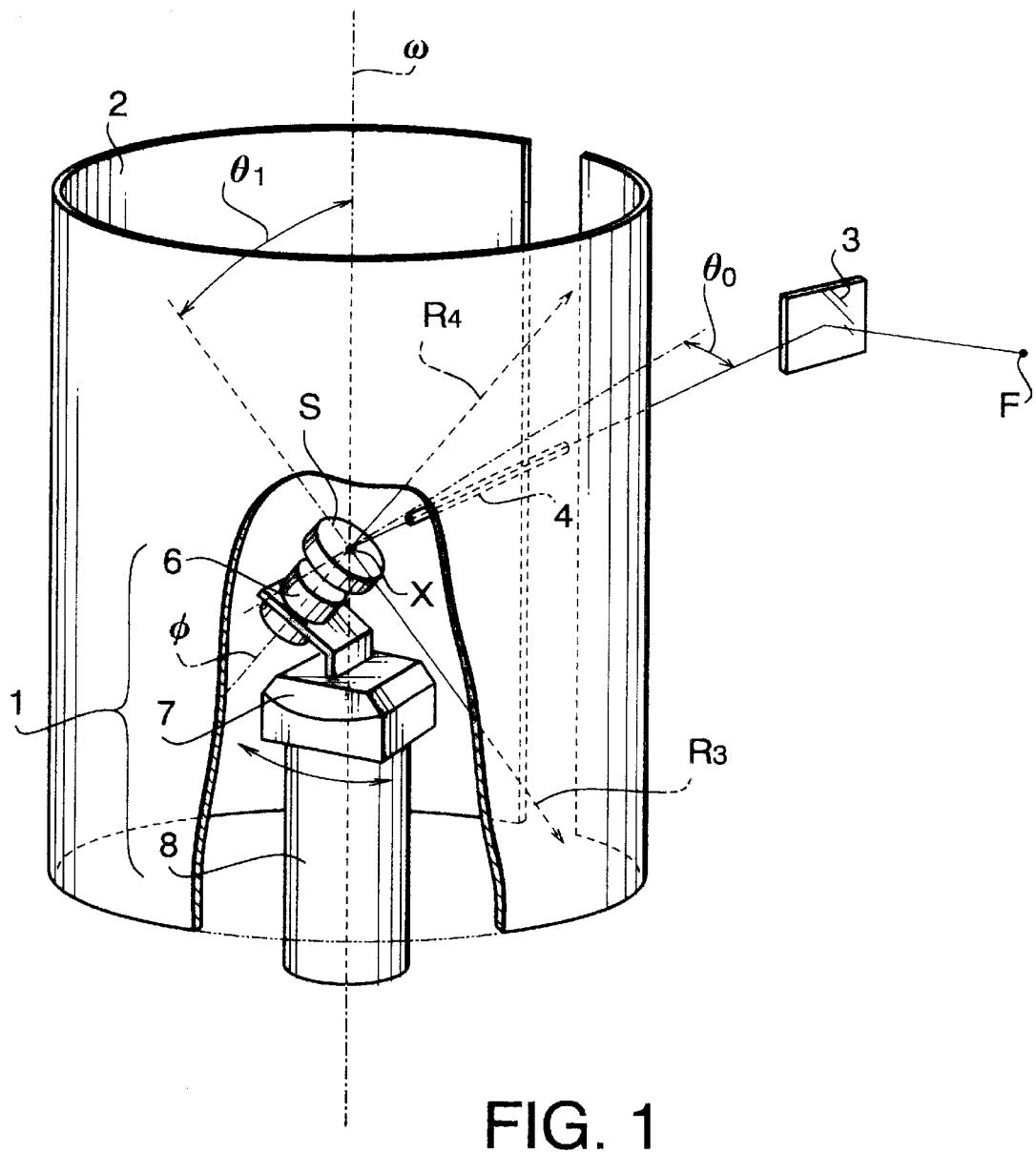
FIG. 1 is a partially cut away, perspective view of an embodiment of an X-ray micro-diffraction apparatus according to the present invention.

FIG. 1 is a partially cut away, perspective view of an embodiment of an X-ray micro-diffraction apparatus for detecting X-ray diffraction of a minute sample portion of a specimen, according to the present invention. The X-ray micro-diffraction apparatus comprises an X-ray focal point 'F' as an X-ray source for emitting X-rays, a monochromator 3 for making X-rays emitted from the X-ray focal point 'F' monochromatic, a collimator 4 for deriving the monochromatic X-rays as a parallel X-ray beam having a minute cross sectional diameter, a specimen support member 1 for supporting a specimen 'S', and a stimulation type fluorescent member 2 as a two-dimensional X-ray detector, which has a cylindrical shape surrounding the specimen 'S'.

Although the specimen 'S' is shown in FIG. 1 in an enlarged scale, it is practically smaller. Further, the X-ray focal point 'F' may be formed as, for example, an X-ray focus of a point type. The monochromator 3 may be constructed with, for example, a flat graphite crystal plate. The collimator 4 forms a parallel X-ray beam having a cross sectional diameter of, for example, 10~100 μm. The stimulation type fluorescent member 2 has an inner surface formed of a fluorescent material.

The specimen support member 1 includes a φ rotary mechanism 6 for rotating the specimen 'S' about an φ axis so as to rotate the specimen 'S' in a plane, a swing mechanism 7 for swinging the specimen 'S' about a center 'X' thereof by a limited angle and an ω rotary mechanism 8 for rotating the specimen 'S' about an ω axis. In this embodiment, the swing mechanism 7 is mounted on the ω rotary mechanism 8 and the φ rotary mechanism 6 is mounted on the swing mechanism 7.

An operation of the X-ray micro-diffraction apparatus constructed as mentioned above will now be described.

Figure 2:
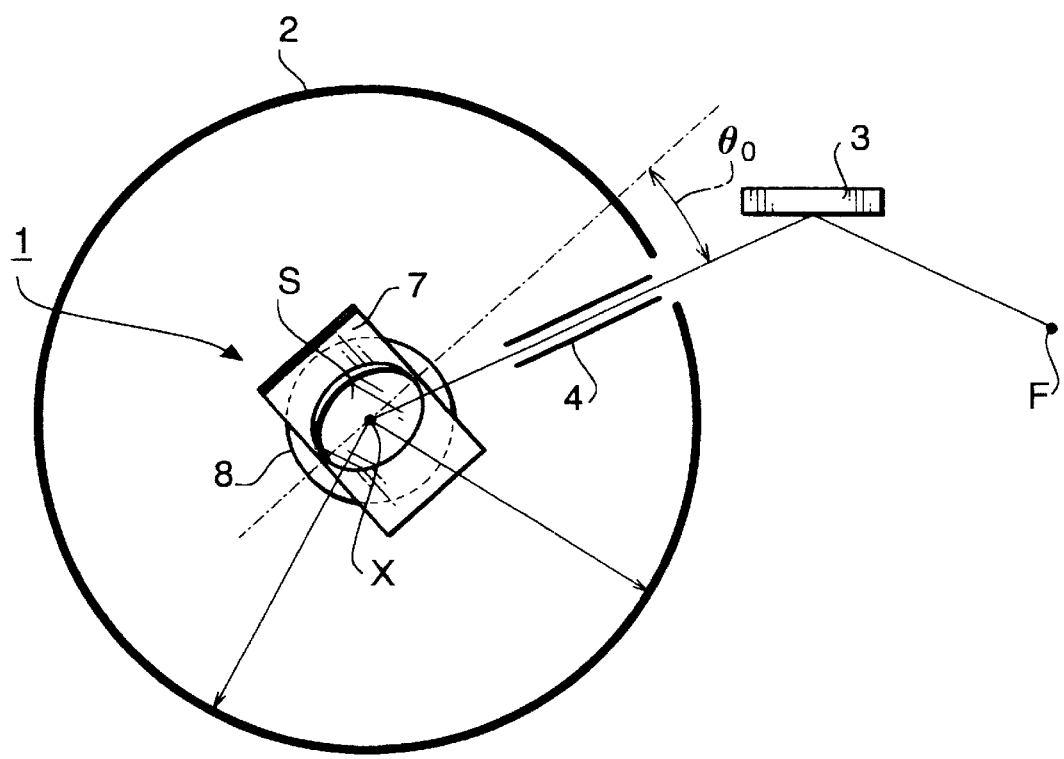
FIG. 2 is a plan view of the X-ray micro-diffraction apparatus shown in FIG. 1.
Figure 3:
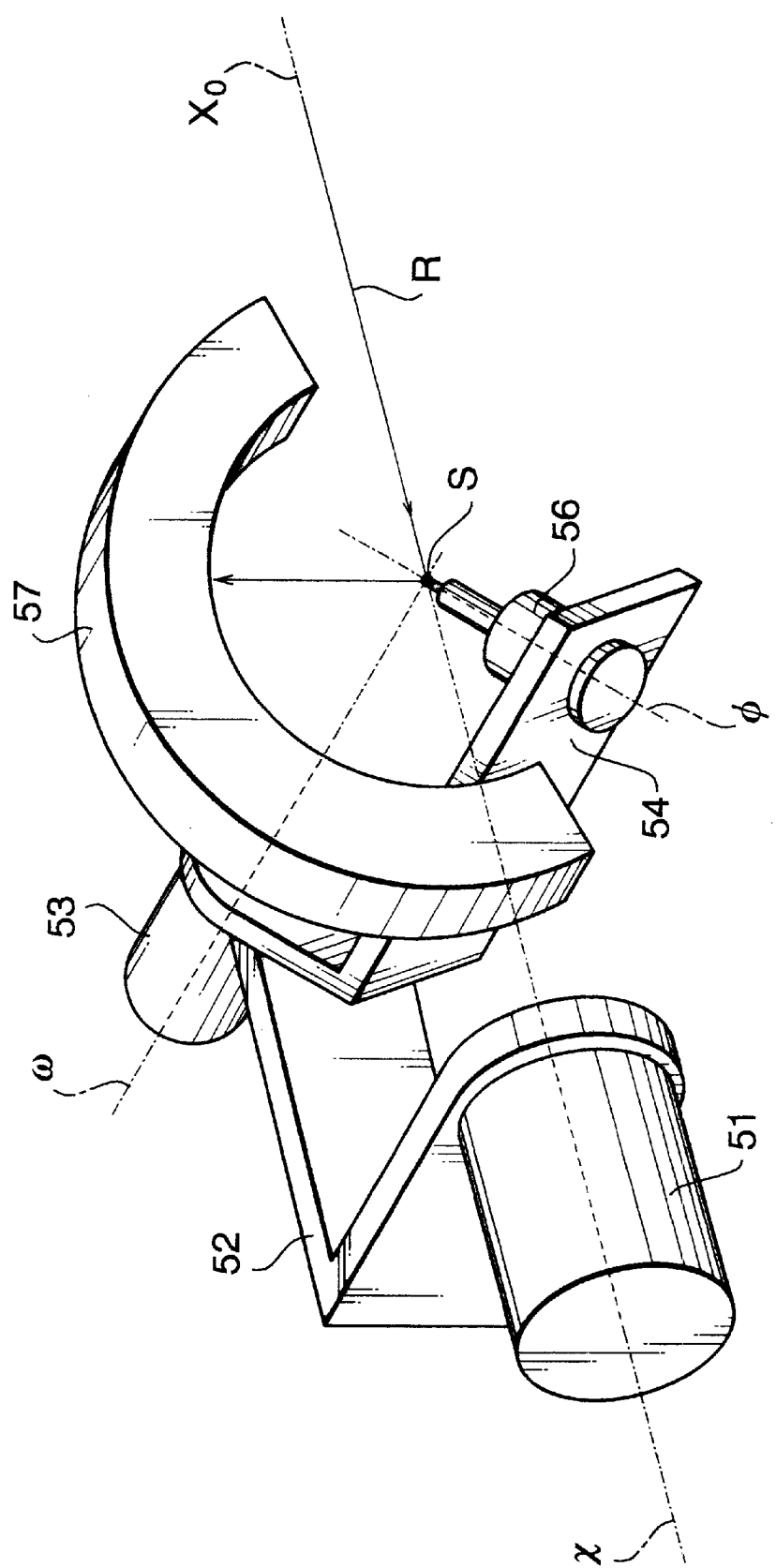
FIG. 3 is a perspective view of an example of a conventional X-ray micro-diffraction apparatus.
Figure 4:
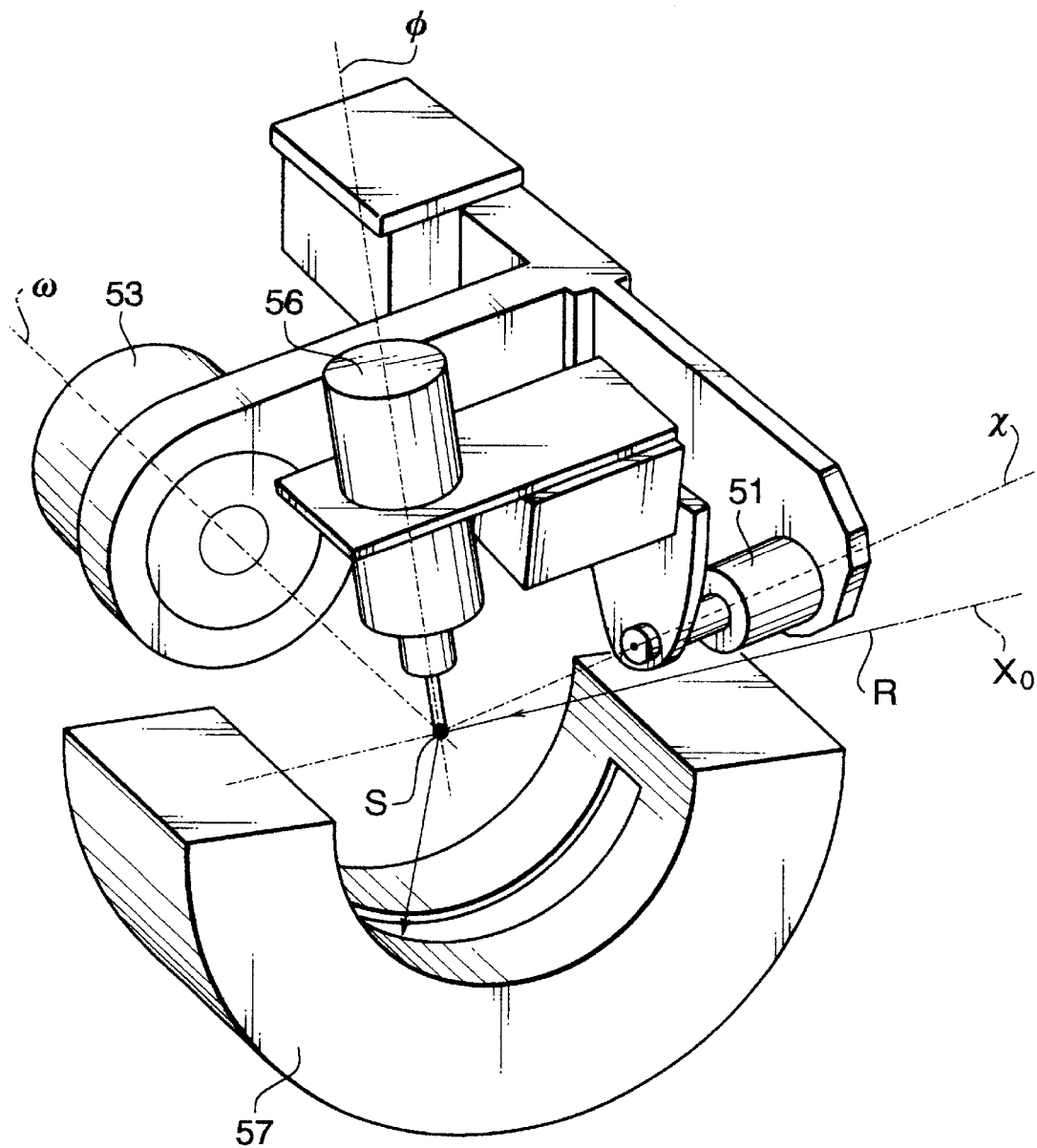
FIG. 4 is a perspective view of another example of a conventional X-ray micro-diffraction apparatus.

First, the cylindrical stimulation type fluorescent member 2 is arranged in such a way that a center axis thereof coincides with the χ axis. Further, the specimen 'S' is mounted on a predetermined position of the φ rotary mechanism 6 of the specimen support member 1. The mounting can be achieved by any known method. Then, as shown in FIG. 2, an incident angle θ0 of the X-rays to the specimen 'S' is set to a predetermined value, for example, 20°~30°, by activating the ω rotary mechanism 8.

Then, as shown in FIG. 1, the swing mechanism 7 is driven such that the sample facet of the specimen 'S' is tilted by a tilting angle θ1, for example, about 45° with respect to the center axis of the stimulation type fluorescent member 2, and hence, the ω axis. This regulation of the tilting angle is performed manually in this embodiment. It should be noted, however, that this regulation could be performed automatically by providing a motor or other drive source on the swing mechanism 7.

The purpose of the tilting of the specimen 'S' by about 45° with respect to the stimulation type fluorescent member 2 is to make the member 2 possible to detect both the diffracted X-rays R3 coming from the specimen 'S' along the direction tangential to the sample facet and the diffracted X-rays R4 coming from the specimen 'S' in the direction perpendicular to the sample facet. In view of the above, in a case where the size of the stimulation type fluorescent member 2 in the axis direction is long enough to detect both the diffracted X-rays R3 coming from the specimen 'S' along the direction tangential to the sample facet and the diffracted X-rays R4 coming from the specimen 'S' in the direction perpendicular to the sample facet even when the tilting angle of the specimen 'S' is deviated from 45°, it is not always necessary to set the tilting angle to 45° exactly.

After completion of settings described above, the X-rays emitted from the X-ray focal point 'F' and passing through both the monochromater 3 and the collimator 4 is passed to the minute sample portion of the specimen 'S' while the specimen 's' is rotated about the φ axis by the φ rotary mechanism 6. At this moment, when the Bragg's diffraction condition is satisfied between the incident X-rays and the crystal lattice face of the specimen 'S', diffraction of the X-rays occurs in the specimen 'S'.

Since the X-rays fall on only the minute sample portion of the specimen 'S', the number of crystal grains contained in the irradiation field is small. Therefore, X-rays diffracted by these crystal grains propagate in a specific diffraction angle. If the zero-dimensional X-ray detector such as the SC or the one-dimensional X-ray detector such as the PSPC is used for receiving such diffracted X-rays, it is necessary to scan, that is, to rotate the X-ray detector about the χ axis. On the contrary, according to this embodiment of the present invention, it is possible to perform the same measurement by rotating the specimen 'S' about only the φ axis.

In the conventional method in which both the rotation of the specimen 'S' about the φ axis and the rotation thereof about the χ axis are necessary, the irradiation field of the X-rays on the specimen 'S' tends to be broadened due to a possible crossing error of the two axes and, therefore, it is difficult to irradiate the minute sample portion of the specimen 'S' with high preciseness. According to the embodiment of the present invention, it is possible to solve the above mentioned problem since there is no need of providing the rotation of the specimen about the χ axis.

In the embodiment mentioned above, since one of the rotary systems for the specimen, namely the χ rotary mechanism, may be removed, the X-ray micro-diffraction apparatus becomes simpler in the structure. Further, since the two-dimensional X-ray detector is used, it is possible to shorten the measuring time compared with the case in which the zero-dimensional or one-dimensional X-ray detector is used alternatively.

(Second Embodiment)

Figure 5:
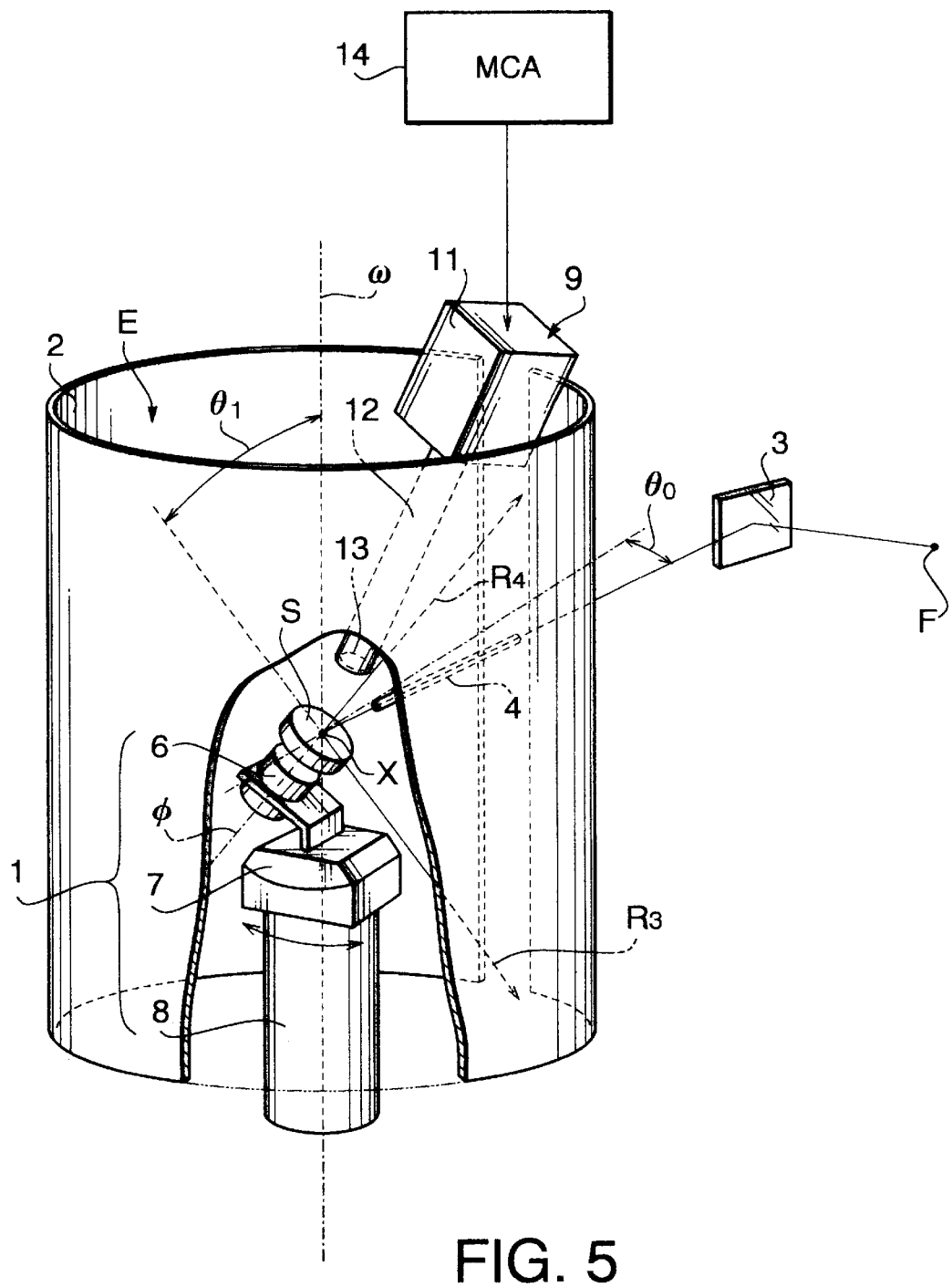
FIG. 5 is a partially cut away, perspective view of another embodiment of an X-ray micro-diffraction apparatus according to the present invention.

FIG. 5 shows another embodiment of the X-ray micro-diffraction apparatus according to the present invention. The second embodiment differs from the X-ray micro-diffraction apparatus shown in FIGS. 1 and 2 in that an X-ray detection unit 9 is arranged in an upper opening 'E' of the edge openings of the cylindrical stimulation type fluorescent member 2.

The X-ray detection unit 9 includes a main body 11 and a cylindrical detecting portion 12, at the forward end of which an SSD 13 is provided. A preamplifier for amplifying an output signal from the SSD 13, a connector for deriving an output signal of the preamplifier externally and a cooling device for cooling the SSD 13, etc., are housed in the main body portion 11. The purpose of the cooling of the SSD 13 and the like is mainly to prevent thermal noise from occurring.

The X-ray detection unit 9 is so arranged not to prevent a progression of both X-rays passed through the collimator 4 to be direct to the specimen 'S' and diffracted X-rays R3 and R4. Further, the SSD 13 should be located at a position that is as close to the sample face of the specimen 'S' as possible and in a plane substantially perpendicular to the sample facet of the specimen 'S'. With being arranged as mentioned above, the SSD 13 can receive fluorescent X-rays within a wide divergence angle.

The SSD 13 receives fluorescent X-rays generated from the specimen 'S' and outputs a pulse signal having a height corresponding to an amount of energy of the fluorescent X-rays. An MCA 14 is connected to the output of the SSD 13. The MCA 14 measures heights, that is, amounts of energy of the respective pulse signals output from the SSD 13 to obtain an energy distribution of the fluorescent X-rays generated from the specimen 'S'. On the basis of the energy distribution thus obtained, it is possible to measure both the kind of atoms existing within the specimen 'S' and the amount thereof.

In the X-ray micro-diffraction apparatus explained above, since the cylindrical stimulation type fluorescent member 2 is used as the X-ray detector, the X-ray detection unit 9 may be arranged in the opening formed at the edge of the cylindrical stimulation type fluorescent member 2 so as to locate the SSD 13 in the vicinity of the specimen 'S'. By this arrangement, the fluorescent X-ray measurement can be performed by using of the SSD 13 while the X-ray micro-diffraction measurement being performed by using of the stimulation type fluorescent member 2. As a result, it becomes possible to perform the analysis of atoms contained in the specimen in addition to the analysis of crystal structure of the specimen.

Arranging the X-ray detection unit 9 in the edge opening of the stimulation type cylindrical fluorescent member 2 makes possible to locate the receiving portion for X-rays of the SSD 13 in the vicinity of the specimen 'S', and besides, at a low angle position with respect to the normal line of the sample face. Therefore, the SSD 13 comes to receive fluorescent X-rays within a large divergence angle. Further, since the path of the X-ray within the specimen 'S' becomes short, the influence of absorption is reduced to perform the fluorescent X-ray analysis efficiently.

(Other Embodiments)

Although the present invention has been described with reference to the preferred embodiments, the present invention is not limited to them and can be variously modified or changed within the scope of the invention defined by the appended claims.

For example, the specimen support device 1 shown in FIG. 1 is a mere example, so a specimen support device having other structure than that described can support the specimen.

What is claimed is:

1. An X-ray micro-diffraction measuring method for detecting X-rays diffracted at a minute portion of a specimen irradiated with X-rays, comprising the steps of arranging a cylindrical two-dimensional X-ray detector surrounding said specimen; and tilting a sample facet of said specimen with respect to said two-dimensional X-ray detector such that both diffracted X-rays passing from said specimen along a direction tangential to said sample facet of said specimen and diffracted X-rays passing from said specimen along a direction perpendicular to said sample facet of said specimen are simultaneously detected by said two-dimensional X-ray detector.

2. An X-ray micro-diffraction measuring method as claimed in claim 1, wherein said two-dimensional X-ray detector is formed by a stimulation type fluorescent member.

3. An X-ray micro-diffraction measuring method as claimed in claim 2, wherein said sample facet of said specimen is tilted with respect to a center axis of said two-dimensional X-ray detector by the angle of about 45°.

4. An X-ray diffraction measuring method as claimed in claim 2, wherein a semiconductor X-ray detector is arranged in an opening formed at the edge of said cylindrical two-dimensional X-ray detector to detect fluorescent X-rays generated by said specimen and wherein said specimen is analyzed on the basis of the detected fluorescent X-rays.

5. An X-ray micro-diffraction measuring method as claimed in claim 1, wherein said sample facet of said specimen is tilted with respect to a center axis of said two-dimensional X-ray detector by the angle of about 45°.

6. An X-ray diffraction measuring method as claimed in claim 5 wherein a semiconductor X-ray detector is arranged in an opening formed at the edge of said cylindrical two-dimensional X-ray detector to detect fluorescent X-rays generated by said specimen and wherein said specimen is analyzed on the basis of the detected fluorescent X-rays.

7. An X-ray diffraction measuring method as claimed in claim 1, wherein a semiconductor X-ray detector is arranged in an opening formed at the edge of said cylindrical two-dimensional X-ray detector to detect fluorescent X-rays generated by said specimen and wherein said specimen is analyzed on the basis of the detected fluorescent X-rays.

8. An X-ray micro-diffraction apparatus for detecting X-rays diffracted at a minute sample portion of a specimen upon irradiating said minute sample portion with X-rays, comprising:

a cylindrical two-dimensional X-ray detector arranged around said specimen;

φ rotary means for rotating said specimen within a plane;

tilting means for tilting a sample facet of said specimen with respect to said two-dimensional X-ray detector; and ω rotary means for rotating said specimen to change an incident angle of X-rays to said specimen.

9. An X-ray micro-diffraction apparatus as claimed in claim 8, wherein said two-dimensional X-ray detector is formed by a stimulation type fluorescent member.

10. An X-ray micro-diffraction apparatus as claimed in claim 9, wherein said tilting means tilts said sample facet of said specimen by the angle of about 45° with respect to a center axis of said stimulation type fluorescent member.

11. An X-ray micro-diffraction apparatus as claimed in claim 9, further comprising a semiconductor X-ray detector arranged in an opening of said cylindrical two-dimensional X-ray detector for receiving fluorescent X-rays and outputting signals corresponding to amounts of energy of the fluorescent X-rays and an energy distribution measuring device responsive to the output signals from said semiconductor X-ray detector for obtaining an energy distribution of the fluorescent X-rays.

12. An X-ray micro-diffraction apparatus as claimed in claim 8, wherein said tilting means tilts said sample facet of said specimen by the angle of about 45° with respect to a center axis of said stimulation type fluorescent member.

13. An X-ray micro-diffraction apparatus as claimed in claim 12, further comprising a semiconductor X-ray detector arranged in an opening of said cylindrical two-dimensional X-ray detector for receiving fluorescent X-rays and outputting signals corresponding to amounts of energy of the fluorescent X-rays and an energy distribution measuring device responsive to the output signals from said semiconductor X-ray detector for obtaining an energy distribution of the fluorescent X-rays.

14. An X-ray micro-diffraction apparatus as claimed in claim 8, further comprising a semiconductor X-ray detector arranged in an opening of said cylindrical two-dimensional X-ray detector for receiving fluorescent X-rays and outputting signals corresponding to amounts of energy of the fluorescent X-rays and an energy distribution measuring device responsive to the output signals from said semiconductor X-ray detector for obtaining an energy distribution of the fluorescent X-rays.

* * * * *

(12) EX PARTE REEXAMINATION CERTIFICATE (5806th)
United States Patent
Dosho

(10) Number: US 6,285,736 C1
(45) Certificate Issued: Jul. 10, 2007

(54) METHOD FOR X-RAY MICRO-DIFFRACTION MEASUREMENT AND X-RAY MICRO-DIFFRACTION APPARATUS

(75) Inventor: Akihide Dosho, Tokyo (JP)

(73) Assignee: Rigaku Corporation, Tokyo (JP)

Reexamination Request:
No. 90/007,140, Jul. 28, 2004

Reexamination Certificate for:
Patent No.: 6,285,736
Issued: Sep. 4, 2001
Appl. No.: 09/427,618
Filed: Oct. 27, 1999

(30) Foreign Application Priority Data

Nov. 13, 1998 (JP) .......................................... 10-323538

(51) Int. Cl.
*G01N 23/20* (2006.01)

(52) U.S. Cl. .............................. 378/79; 378/71; 378/73; 378/81; 378/83

(58) Field of Classification Search ................... 378/46, 378/70, 71, 73, 79, 81, 83
See application file for complete search history.

(56) References Cited

FOREIGN PATENT DOCUMENTS

| | | |
|---|---|---|
| GB | 2050780 A | 1/1981 |
| JP | 9061380 A | 3/1997 |
| WO | WO93/08462 | 4/1993 |
| WO | WO94/15202 | 7/1994 |

*Primary Examiner*—Edward J. Glick

(57) ABSTRACT

An X-ray micro-diffraction measuring method for detecting X-rays diffracted at a minute portion of a specimen upon irradiating the minute portion with X-rays is disclosed. A cyclindrical stimulation type fluorescent member is arranged around the specimen. A sample facet of the specimen is tilted by, for example, 45° with respect to the stimulation type fluorescent member such that the stimulation type fluorescent member can receive both diffracted X-rays passing along a direction tangential to the sample facet and diffracted X-rays passing along a direction perpendicular to the sample facet. Diffracted X-ray images can be obtained on the stimulation type fluorescent by merely rotating the specimen about only the Φ axis thereof so as to perform the in-plane rotation without a rotation about the χ axis. By eliminating a rotation about one axis from rotations about two axes for the specimen, it may be possible to avoid a degradation of measurement preciseness due to a crossing error of the two axes. Also, the elimination of the axis mentioned above may cause the structure of the apparatus to be simplified and the time required for the measurement to be shortened.

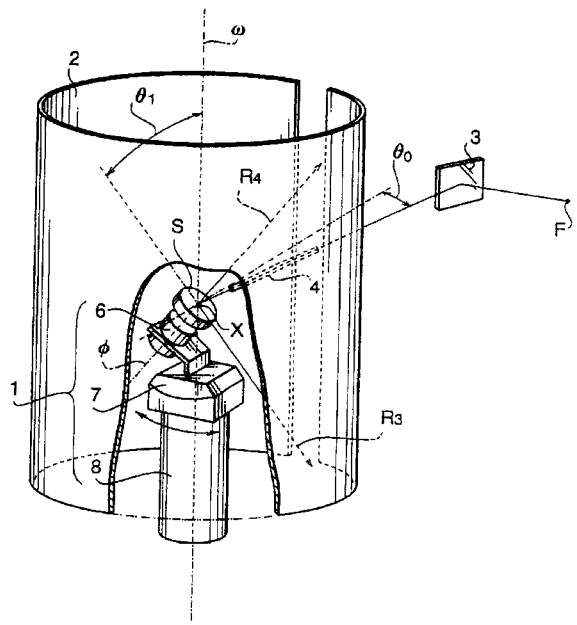
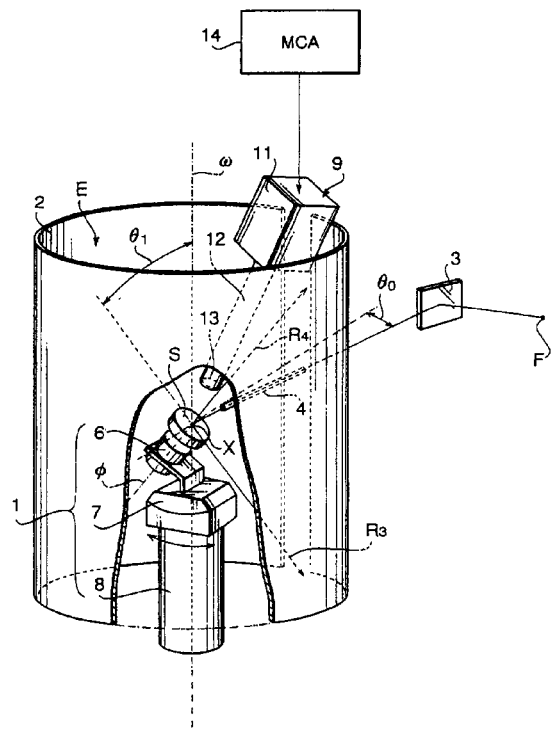

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 6, 7 and 8 are determined to be patentable as amended.

Claims 2-3, 5 and 9-14, dependent on an amended claim, are determined to be patentable.

1. An X-ray micro-diffraction measuring method for detecting X-rays diffracted at a minute portion of a specimen irradiated with X-rays, comprising the steps of:
   arranging *said specimen in* a cylindrical two-dimensional X-ray detector surrounding said specimen, *the center axis of said detector coinciding with an ω axis which passes through said specimen*; and
   irradiating a sample facet of said specimen with X-rays which travel laterally relative to the center axis of said detector;
   tilting a sample facet of said specimen with respect to said two-dimensional X-ray detector such that both diffracted X-rays passing from said specimen along a direction tangential to said sample facet of said specimen and diffracted X-rays passing from said specimen along a direction perpendicular to said sample facet of said specimen are simultaneously detected by said two-dimensional X-ray detector;
   *said sample facet being tilted relative to the center axis of said detector and said specimen being rotated about a Φ axis to rotate said sample facet in its own plane during the irradiation of said sample facet.*

4. An X-ray *micro-*diffraction measuring method as claimed in claim 2, wherein a semiconductor X-ray detector is arranged in an opening formed at the edge of said cylindrical two-dimensional X-ray detector to detect fluorescent X-rays generated by said specimen and wherein said specimen is analyzed on the basis of the detected fluorescent X-rays.

6. An X-ray *micro-*diffraction measuring method as claimed in claim 5 wherein a semiconductor X-ray detector is arranged in an opening formed at the edge of said cylindrical two-dimensional X-ray detector to detect fluorescent X-rays generated by said specimen and wherein said specimen is analyzed on the basis of the detected fluorescent X-rays.

7. An X-ray *micro-*diffraction measuring method as claimed in claim 1, wherein a semiconductor X-ray detector is arranged in an opening formed at the edge of said cylindrical two-dimensional X-ray detector to detect fluorescent X-rays generated by said specimen and wherein said specimen is analyzed on the basis of the detected fluorescent X-rays.

8. An X-ray micro-diffraction apparatus for detecting X-rays diffracted at a minute sample portion of a specimen upon irradiating said minute sample portion with X-rays, comprising:
   a cylindrical two dimensional X-ray detector arranged around said specimen;
   *means for supporting said specimen within said detector such that an ω axis which passes through said specimen coincides with the center axis of said detector; and*
   *means for irradiating a sample facet of said specimen with X-rays which are arranged to travel laterally relative to the center axis of said detector;*
   *said means for supporting said specimen including:*
   Φ rotary means for rotating said specimen within a plane *whereby a sample facet is rotated in its own plane*;
   tilting means for tilting [a] *the* sample facet of said specimen with respect to *the center axis of* said two-dimensional X-ray detector; [and]
   ω rotary means for rotating said specimen to change an incident angle of X-rays to said specimen;
   *whereby said detector, said supporting means and said irradiating means are arrangeable such that diffracted X-rays passing from said specimen along a direction tangential to said sample facet of said specimen and diffracted X-rays passing from said specimen along a direction perpendicular to said sample facet of said specimen are simultaneously detectable by said detector.*

\* \* \* \* \*